United States Patent
Thomas et al.

(10) Patent No.: US 10,399,078 B2
(45) Date of Patent: Sep. 3, 2019

(54) BIASED SAMPLE INJECTION FLOW CELL

(71) Applicant: Beckman Coulter, Inc., Brea, CA (US)

(72) Inventors: Richard A. Thomas, Miami, FL (US); Charles C. Wong, Rancho Palos Verdes, CA (US); Christopher Delametter, Noblesville, IN (US); Andrew M. Hardie, Davie, FL (US)

(73) Assignee: Beckman Coulter, Inc., Brea, CA (US)

( * ) Notice: Subject to any disclaimer, the term of this patent is extended or adjusted under 35 U.S.C. 154(b) by 150 days.

(21) Appl. No.: 15/316,078

(22) PCT Filed: Jun. 5, 2015

(86) PCT No.: PCT/US2015/034386
§ 371 (c)(1),
(2) Date: Dec. 2, 2016

(87) PCT Pub. No.: WO2015/188050
PCT Pub. Date: Dec. 10, 2015

(65) Prior Publication Data
US 2017/0106368 A1    Apr. 20, 2017

Related U.S. Application Data

(60) Provisional application No. 62/009,082, filed on Jun. 6, 2014.

(51) Int. Cl.
*B01L 3/00* (2006.01)
*G01N 15/14* (2006.01)
(Continued)

(52) U.S. Cl.
CPC ... *B01L 3/502715* (2013.01); *B01L 3/502761* (2013.01); *G01N 15/1404* (2013.01);
(Continued)

(58) Field of Classification Search
CPC ........... G01N 15/1459; G01N 15/1456; G01N 15/14; G01N 15/10; G01N 21/51;
(Continued)

(56) References Cited

U.S. PATENT DOCUMENTS

| 4,564,803 | A | * | 1/1986 | Loren ................ G01N 15/1218 134/36 |
| 4,673,288 | A | * | 6/1987 | Thomas ............. G01N 15/1218 324/71.4 |

(Continued)

FOREIGN PATENT DOCUMENTS

| EP | 0279000 A1 | 8/1988 |
| JP | 02-17652 | 9/1990 |
| JP | 2007-003474 A | 1/2007 |

OTHER PUBLICATIONS

International Search Report and Written Opinion for PCT/US2015/034386, dated Sep. 9, 2015.

*Primary Examiner* — Christine T Mui
(74) *Attorney, Agent, or Firm* — Merchant & Gould P.C.

(57) ABSTRACT

Apparatuses, components, methods, and systems for interrogating samples are provided. An example system includes a flow cell. An example flow cell includes an aperture, an inlet chamber, and a sample injector positioned within the inlet chamber. An example sample injector is configured to generate a sample stream that flows in biased proximity to a profile included in the inlet chamber. An example method includes the steps of causing sheath fluid to flow into an inlet chamber and through an aperture, injecting sample into an inlet chamber with a sample injector to form a sample stream that is entrained in the sheath fluid, and interrogating the sample stream as the sample stream passes through an interrogation region within the aperture. An example sample injector includes an outlet that is disposed in an off-center position within the inlet chamber.

20 Claims, 11 Drawing Sheets (51) Int. Cl.
    *G01N 21/51*     (2006.01)
    *G01N 15/10*     (2006.01)
    *G01N 15/12*     (2006.01)
    *G01N 15/00*     (2006.01)

(52) U.S. Cl.
    CPC .... *G01N 15/1484* (2013.01); *B01L 2200/027* (2013.01); *B01L 2200/0636* (2013.01); *B01L 2200/0647* (2013.01); *B01L 2200/14* (2013.01); *B01L 2300/0858* (2013.01); *G01N 2015/0065* (2013.01); *G01N 2015/1236* (2013.01); *G01N 2015/1409* (2013.01); *G01N 2015/1413* (2013.01)

(58) Field of Classification Search
    CPC ........ G01N 21/49; G01N 21/47; G01N 21/17; B01L 3/502715; B01L 3/5027; B01L 3/502; B01L 3/50
    USPC .............................. 422/502, 500, 50; 356/72
    See application file for complete search history.

(56) References Cited

U.S. PATENT DOCUMENTS

| | | | |
|---|---|---|---|
| 4,818,103 A * | 4/1989 | Thomas | G01N 15/1218 324/71.4 |
| 4,954,715 A | 9/1990 | Zöld | |
| 5,561,517 A * | 10/1996 | Horiuchi | G01N 15/14 356/39 |
| 2007/0085997 A1 | 4/2007 | Thomas | |

* cited by examiner

BIASED SAMPLE INJECTION FLOW CELL

CROSS-REFERENCE TO RELATED APPLICATION(S)

This application is a U.S. National Stage application of PCT/US2015/034386, filed Jun. 5, 2015, which claims benefit of U.S. Provisional Patent Application Ser. No. 62/009,082, filed Jun. 6, 2014, and which applications are hereby incorporated by reference in their entireties. To the extent appropriate, a claim of priority is made to each of the above disclosed applications.

BACKGROUND

In a flow cytometer, sample particles are passed through a small aperture in a flow cell (sometimes referred to as a measuring chamber). The small aperture confines the particles to an interrogation zone or region where they can then be evaluated.

In a particle analyzer, for example a flow cytometer, particles such as cells arranged in a sample stream pass through one or more excitation light beams with which the particles interact. Light scattered or emitted by the particles upon interaction with the one or more excitation beams is collected, detected, and analyzed to characterize and differentiate the particles. For example, forward scattering of an excitation beam along its axis may provide information about particle size, side scattering of an excitation beam orthogonally to its axis may provide information about particle internal structure or internal complexity, and fluorescence excited by the one or more excitation beams may provide information about the presence or absence in the particles of fluorophores correlating with particular chemical or biological properties of the particles.

The performance of the analyzer is affected by the proper spatial alignment and positioning of the particles in the sample stream as they pass through the interrogation region. For example, it is desirable to have the particles in a linear arrangement so that the particles will pass one-by-one through the interrogation region where the excitation light will impinge on the particles. If two or more particles are introduced into the interrogation region at the same time, an errant measurement may result as the multiple particles may be interpreted as a single particle. Also, it is desirable to have the particles travel in a spatially consistent path so that the focal point of the excitation light may consistently interrogate each particle. Spatial variation in the transverse direction can cause a reduction in the measurement resolution of the analyzer.

Many conventional analyzers attempt to align particles entrained in the sample stream by hydrodynamic focusing. In hydrodynamic focusing, a suspension of particles is injected into the center of a laminar sheath fluid flow. The forces of the sheath fluid confine the sample stream to a narrow core, thereby aligning the particles entrained therein. Although this technique is commonly used, the sample stream rate of conventional flow cytometers is typically between 10-30 μL/min in order to maintain acceptable measurement resolution. A higher stream rate causes the sample stream core to increase thereby increasing the spatial variation of the particles in the transverse direction. The decrease in spatial reproducibility within the interrogation zone results in loss of the analyzer's measurement resolution.

Other attempts to focus the sample stream have been made. One method is to reduce the diameter of the sample injector thereby narrowing the sample stream core before injecting the stream into the middle of the laminar sheath flow. However, one shortcoming of this technique is that the system is prone to clogging the sample injector, which is undesirable. Another existing method to focus the sample stream is to use ultrasonic waves to focus the particles. Such techniques, however, add complexity to the system.

Accordingly, there is a need for an improved flow cell and method to align particles in a flow cell that improves flow stream rate while maintaining measurement resolution. Additional benefit of the improved device and method may be to avoid adding complexity or increasing potential for clogging the system.

SUMMARY

A first aspect is a flow cell comprising: an aperture; an inlet chamber in fluid communication with the aperture, the inlet chamber including a profile, the inlet chamber suitable to contain sheath fluid; and a sample injector disposed in the inlet chamber to inject a sample into the inlet chamber, the injected sample forming a sample stream, the sample injector positioned such that the sample stream travels in biased proximity to the profile; wherein, the sample stream and sheath fluid in the inlet chamber flow through the aperture.

Another aspect is the flow cell of the first aspect, wherein the profile of the inlet chamber includes two planes arranged to form an edge formed by the apex of the two planes.

Another aspect is the flow cell of the first aspect, wherein the profile of the inlet chamber is a recessed V-groove disposed in a surface of the inlet chamber.

Another aspect is the flow cell of the first aspect, wherein the profile of the inlet chamber is a channel formed along a surface of the inlet chamber. In another aspect, the channel has a rectangular cross section. In yet another aspect, the channel has a segment of a circular cross section.

Another aspect is the flow cell of the first aspect, wherein the profile is an interior wall of the inlet chamber.

Another aspect is the flow cell of the first aspect, wherein the profile of the inlet chamber is a feature formed by protrusions on the interior wall of the inlet chamber.

Another aspect is the flow cell of the first aspect, wherein the profile of the inlet chamber is a V-groove formed between protrusions on a surface of the inlet chamber.

Another aspect is the flow cell of the first aspect, wherein the profile extends to the aperture.

Another aspect is the flow cell of the first aspect, wherein the sample includes particles suspended in fluid.

Another aspect is the flow cell of the first aspect, wherein an outlet of the sample injector is positioned between 1650 microns to 1850 microns from an inlet of the aperture.

Another aspect is the flow cell of the first aspect, wherein an outlet of the sample injector is positioned between 1400 microns to 2200 microns from an inlet of the aperture.

Another aspect is the flow cell of the first aspect, wherein an outlet of the sample injector is positioned between 700 microns to 900 microns from the profile.

Another aspect is the flow cell of the first aspect, wherein an outlet of the sample injector is positioned between 400 microns and 1200 microns from the profile.

Another aspect is the flow cell of the first aspect, wherein the sample injector is positioned asymmetrically in the inlet chamber and biased in the direction of the profile.

Another aspect is the flow cell of the first aspect, wherein the sample stream flows through the aperture at least partially oblique to a longitudinal axis of the aperture.

Another aspect is the flow cell of the first aspect, wherein a rate of the sample stream is 70 microliters per minute.

Another aspect is the flow cell of the first aspect, wherein e inlet chamber a conical funnel.

Another aspect is the flow cell of the first aspect, wherein the inlet chamber is generally a three sided pyramidal configuration.

Another aspect is the flow cell of the first aspect, wherein the inlet chamber is a tapered configuration.

Another aspect is the flow cell of the first aspect, wherein a shape of a cross section of the aperture is one of circular, triangular, square, and rectangular.

Another aspect is the flow cell of the first aspect further comprising a plurality of sample injectors.

In another aspect, the plurality of sample injectors are positioned such that the sample stream injected from at least one of the plurality of sample injectors travel in biased proximity to the profile. Yet another aspect, further includes a plurality of profiles, wherein a first sample injector is positioned such that a sample stream injected therefrom travels in biased proximity to a first profile, and a second sample injector is positioned such that a sample stream injected therefrom travels in biased proximity to a second profile. In still another, the plurality of sample injectors are positioned such that the sample streams injected from the plurality of sample injectors share at least a portion of a path within the aperture.

A second aspect is a flow cell comprising: an aperture; an inlet chamber in fluid communication with the aperture; and a sample injector disposed in the inlet chamber to inject a sample into the inlet chamber, the injected sample forming a sample stream, the sample injector positioned off-center within the inlet chamber.

Another aspect is the flow cell of the second aspect, wherein the sample stream flows through the aperture at least partially oblique to the longitudinal axis of the aperture.

Another aspect is the flow cell of the second aspect, wherein the sample includes particles suspended in fluid.

Another aspect is the flow cell of the second aspect, wherein the sample injector is positioned such that the sample stream travels in biased proximity to a profile disposed in the inlet chamber. In yet another aspect, the profile of the inlet chamber includes two planes arranged to form an edge formed by the apex of the two planes. In still another aspect, the profile of the inlet chamber is a V-groove disposed in the inlet chamber surface, in yet another aspect, the profile of the inlet chamber is a feature formed by protrusions on the interior wall of the inlet chamber. In still another aspect, the profile of the inlet chamber is a channel along the inlet chamber surface. In yet another aspect, the profile is an interior wall of the inlet chamber. In still another aspect, wherein the sample injector is positioned between 700 microns to 900 microns from the profile. In yet another aspect, wherein an outlet of the sample injector is positioned between 400 microns and 1200 microns from the profile.

Another aspect is the flow cell of the second aspect, wherein the sample injector is positioned between 1650 microns to 1850 microns from inlet of the aperture.

Another aspect is the flow cell of the second aspect, wherein an outlet of the sample injector is positioned between 1400 microns to 2200 microns from the inlet of the aperture.

Another aspect is the flow cell of the second aspect, wherein rate of sample stream is 70 microliters per minute.

Another aspect is the flow cell of the second aspect, wherein the inlet chamber is generally a three sided pyramidal configuration.

Another aspect is the flow cell of the second aspect, wherein the inlet chamber is a tapered configuration.

Another aspect is the flow cell of the second aspect, wherein the aperture cross section is one of circular, triangular, and rectangular cross section.

Another aspect is the flow cell of the second aspect further comprising a plurality of sample injectors. In yet another aspect, the plurality of sample injectors are positioned such that the sample stream injected from at least one of the plurality of sample injectors travel in biased proximity to the profile. Still another aspect further includes a plurality of profiles, wherein a first sample injector is positioned such that the sample stream injected therefrom travels in biased proximity to a first profile, and a second sample injector is positioned such that the sample stream injected therefrom travels in biased proximity to a second profile. In yet another aspect, the plurality of sample injectors are positioned such that the sample stream injected from the plurality of sample share at least a portion of a path within the aperture.

A third aspect is a method of interrogating a sample comprising: causing sheath fluid to flow into an inlet chamber and through an aperture; injecting the sample into the inlet chamber with a sample injector to form a sample stream that is entrained in the sheath fluid, wherein an outlet of the sample injector is disposed in an off-center position within the inlet chamber; interrogating the sample stream as the sample stream passes through an interrogation region within the aperture.

Another aspect is the method of the third aspect, wherein the outlet of the sample injector is biased in a direction of a profile of the inlet chamber. In yet another aspect, the outlet of the sample injector is biased in a direction of a profile of the inlet chamber and the outlet of the second sample injector is biased in a direction of a second profile of the inlet chamber.

Another aspect is the method of the third aspect further comprising: injecting a second sample into an inlet chamber with a second sample injector to form a second sample stream that is entrained in the sheath fluid, wherein an outlet of the second sample injector is disposed in an off-center position within the inlet chamber; and interrogating the second sample stream as the second sample stream passes through the interrogation region within the aperture.

DETAILED DESCRIPTION

Various embodiments will be described in detail with reference to drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Figure 1:
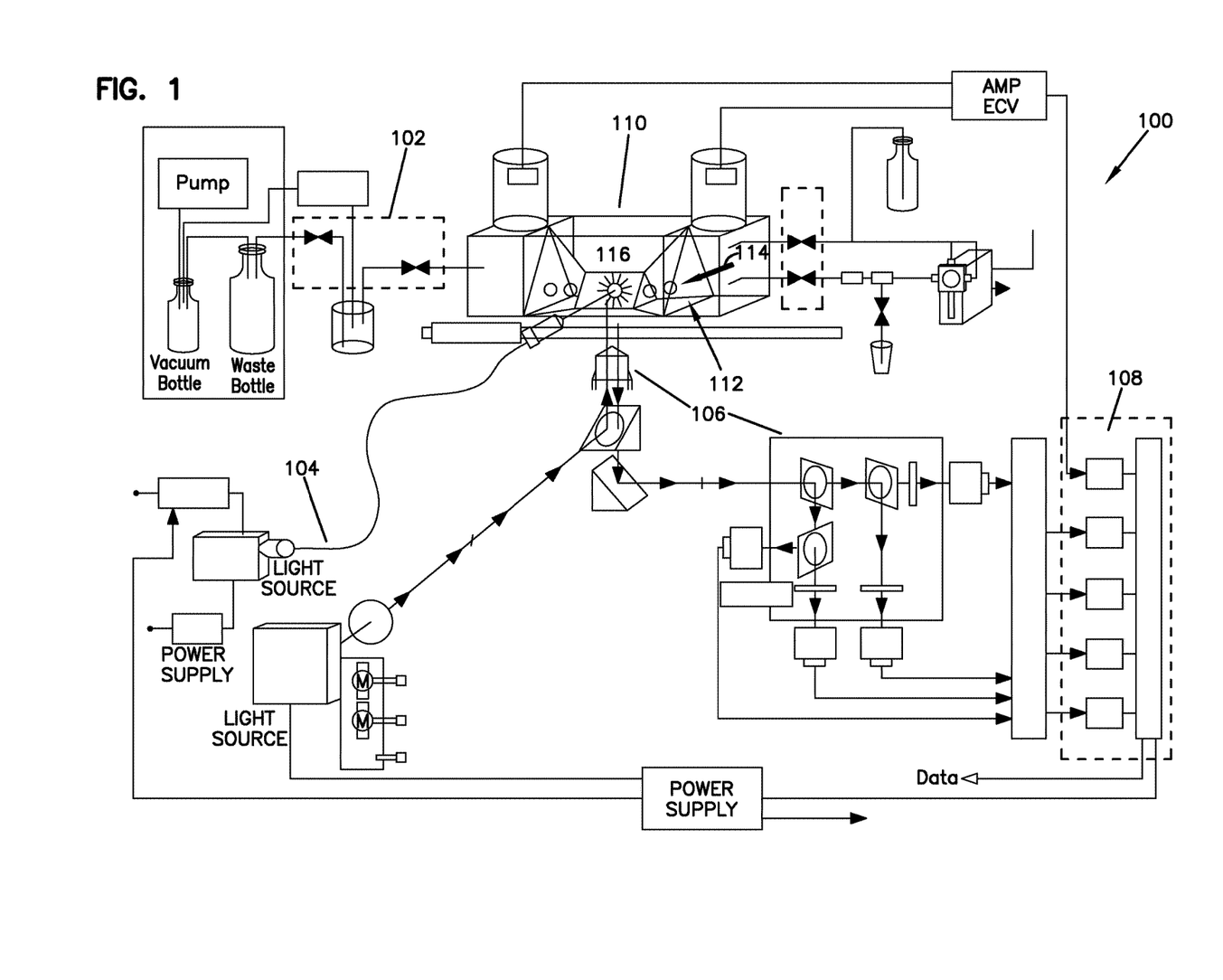
FIG. 1 illustrates an embodiment of a flow cytometer.

As shown in FIG. 1, an embodiment of a flow cytometer 100 includes a fluidics module 102, an illumination optics module 104, a detection optics module 106, an analysis module 108, and a flow cell 110. The flow cell 110 includes an inlet chamber 112, a sample injector 114, and an aperture 116. The fluidics module 102 includes fluid pathways, pumps, and other aspects to transport various fluids throughout the flow cytometer 100. The illumination optics module 104 includes a light source and optical elements to deliver a focused beam of light to the flow cell 110 to interrogate particles passing through the aperture 116 in the flow cell 110. An example light source is a laser that generates a laser beam. Another example light source is an arc lamp. The detection optics module 106 includes optical elements and one or more detectors to detect light signals scattered or emitted from a particle interacting with the beam of light in the flow cell 110. Examples of detectors include photoresists and may include an accompanying light source, such as a mercury lamp. The analysis module 108 includes hardware and software to quantify the detected signals and to characterize properties of the particles based on the quantified signals.

A sample may be any fluid. In some instances, the sample may include particles, such as cells or beads or other like matters, suspended in the fluid. The sample may be in the form of whole blood, or prepared sample, such as lysed blood, labeled particles in suspension, bead assays, immunology stained blood, or DNA stained cells, achieved commonly by adding reagents and performing protocols as commonly known in the art. The sample may be loaded into the flow cytometer 100 in a tube, a plate having multiple wells, or other suitable containers. A sample ingestion device, such as an aspiration probe, may be used to interface the sample. The fluidics module 102 can then transport the sample to a sample injector 114 of the flow cell 110.

Sheath fluid, which may be saline solution, deionized water, or other suitable carrier, may be held in a reservoir accessible by the fluidics module 102. The fluidics module 102 transports the sheath fluid to the inlet chamber 112 of the flow cell.

Figure 2:
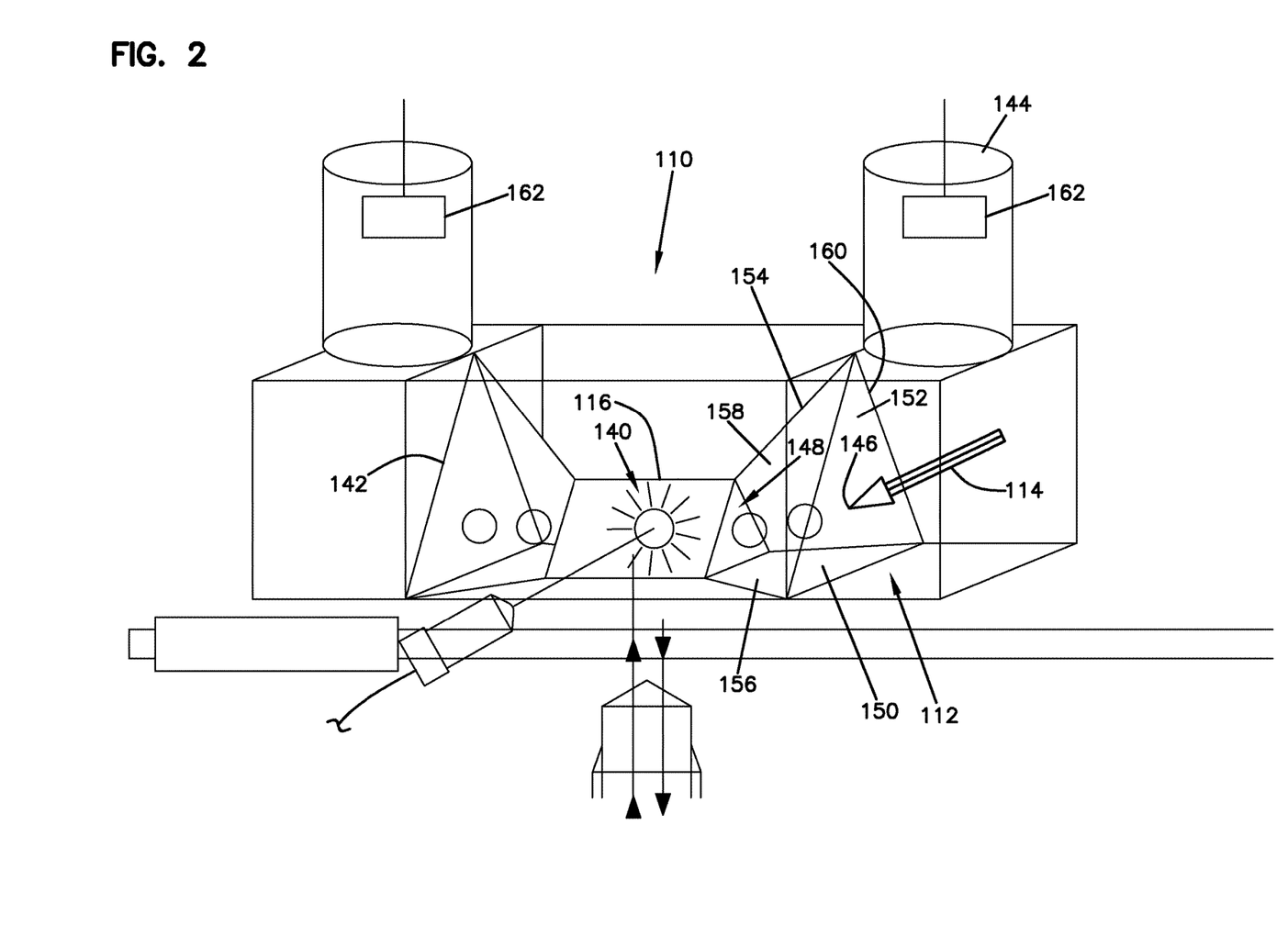
FIG. 2 illustrates an embodiment of the flow cell of FIG. 1.

FIG. 2 illustrates an embodiment of the flow cell 110 that focuses the particles of the sample by narrowing the sample stream core and delivers the sample stream to an interrogation region 140 in the aperture 116. The flow cell 110 includes the inlet chamber 112, a sample injector 114, an aperture 116, and an optional outlet chamber 142. The inlet chamber 112 includes an access point 144 to receive sheath fluid, and the sheath fluid is motivated by the fluidics module 102 (not shown) to flow from the inlet chamber 112 and through the aperture 116. The sample injector 114 includes an outlet 146 and is disposed in the inlet chamber 112. When the sample is discharged or injected into the inlet chamber 112 through the outlet 146, a sample stream is formed. The sample stream then travels out the inlet chamber 112 and into an inlet 148 of the aperture 116. Thus, arranged as described, the sample stream and sheath fluid together travel through the aperture 116 and the interrogation region 140 therein, so that the particles entrained in the sample stream can be interrogated.

As shown in FIG. 2, the inlet chamber is in fluid communication with aperture 116. Inlet chamber 112 receives the sample and sheath fluid and delivers the sample stream to the aperture 116. The inlet chamber 112 includes a cavity 150, at least one interior wall 152, at least one profile 154, and at least one sample injector 114.

In some embodiments, the cavity 150 of the inlet chamber 112 is formed by a bottom surface 156, a first side surface 158, and a second side surface 160 to create a three-sided pyramidal configuration. In some embodiments, each of the surfaces 156, 158, and 160 have a truncated triangular shape. The first side surface 158 and the second side surface 160 are arranged to form a profile 154(a), which is in this embodiment a V-shaped edge formed by the apex of the adjoining surfaces. The profile 154(a) in this embodiment leads to the aperture 116.

In one embodiment, as shown in FIG. 2, the flow cell includes electrodes 162 positioned across the aperture to measure the volume or opacity of the particle passing through the aperture using the Coulter Principle. In this embodiment, the length of the aperture may be 100 to 150 microns.

Figure 3:
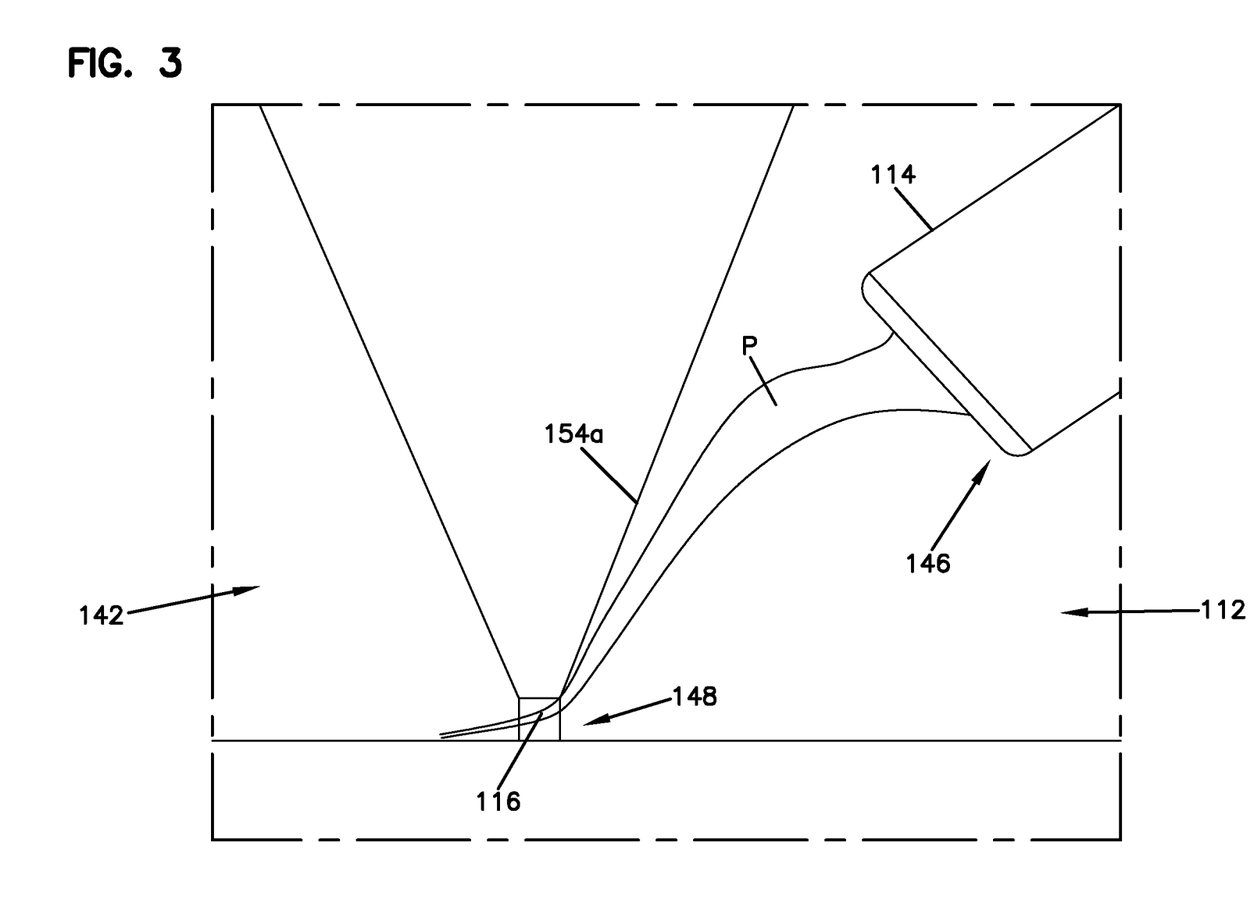
FIG. 3 illustrates an example sample stream flow in biased proximity to an embodiment of a profile of the inlet chamber of FIG. 2.
Figure 4:
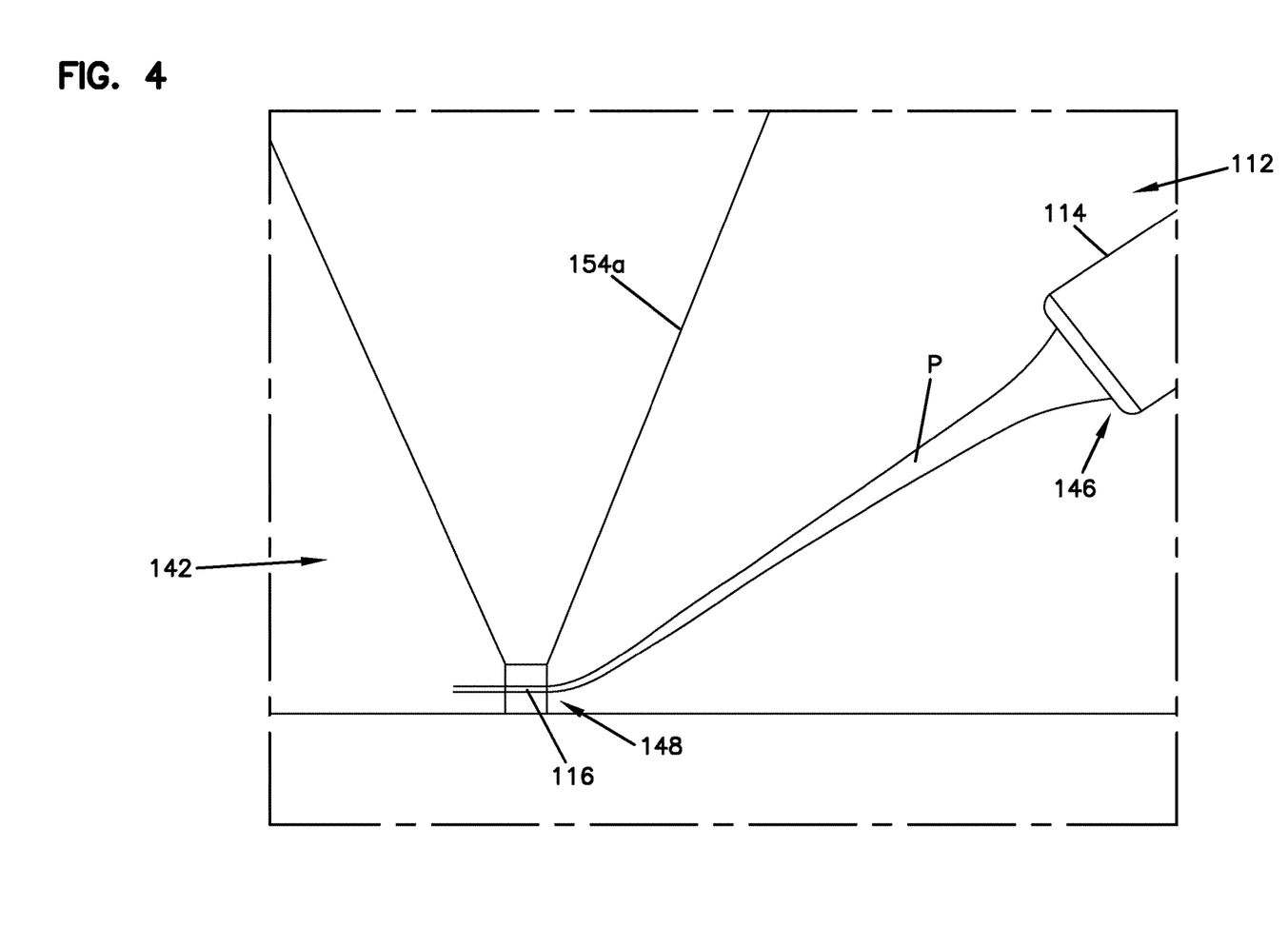
FIG. 4 illustrates an example sample stream flow from a sample injector centrally disposed in an embodiment of the inlet chamber of FIG. 2.

In some embodiments, the outlet 146 of the sample injector 114 is positioned off-center or asymmetrically in the inlet chamber 112, and biased in the direction of the profile 154(a). For example, the sample injector 114 is biased in the direction of the profile 154(a) when the outlet 146 is disposed at a position that is closer than the center of the inlet chamber 112 to the profile 154(a). Referring to FIG. 3, when the outlet 146 of the sample injector 114 is positioned proximate to the profile 154(a), the flow path P of the sample stream from the sample injector 114 tends to travel in along the profile 154(a). This sample stream travels in biased proximity to the profile because of the position of the sample injector. The stream path is biased because it tends to favor travelling in proximity to the profile relative to other areas of the inlet chamber 112. In contrast, as shown in FIG. 4, where the sample injector is positioned generally central to the inlet chamber 112, as commonly arranged in conventional flow cells, the flow path P of the sample stream travels directly to the aperture without bias to other features of the inlet chamber 112.

Figure 5:
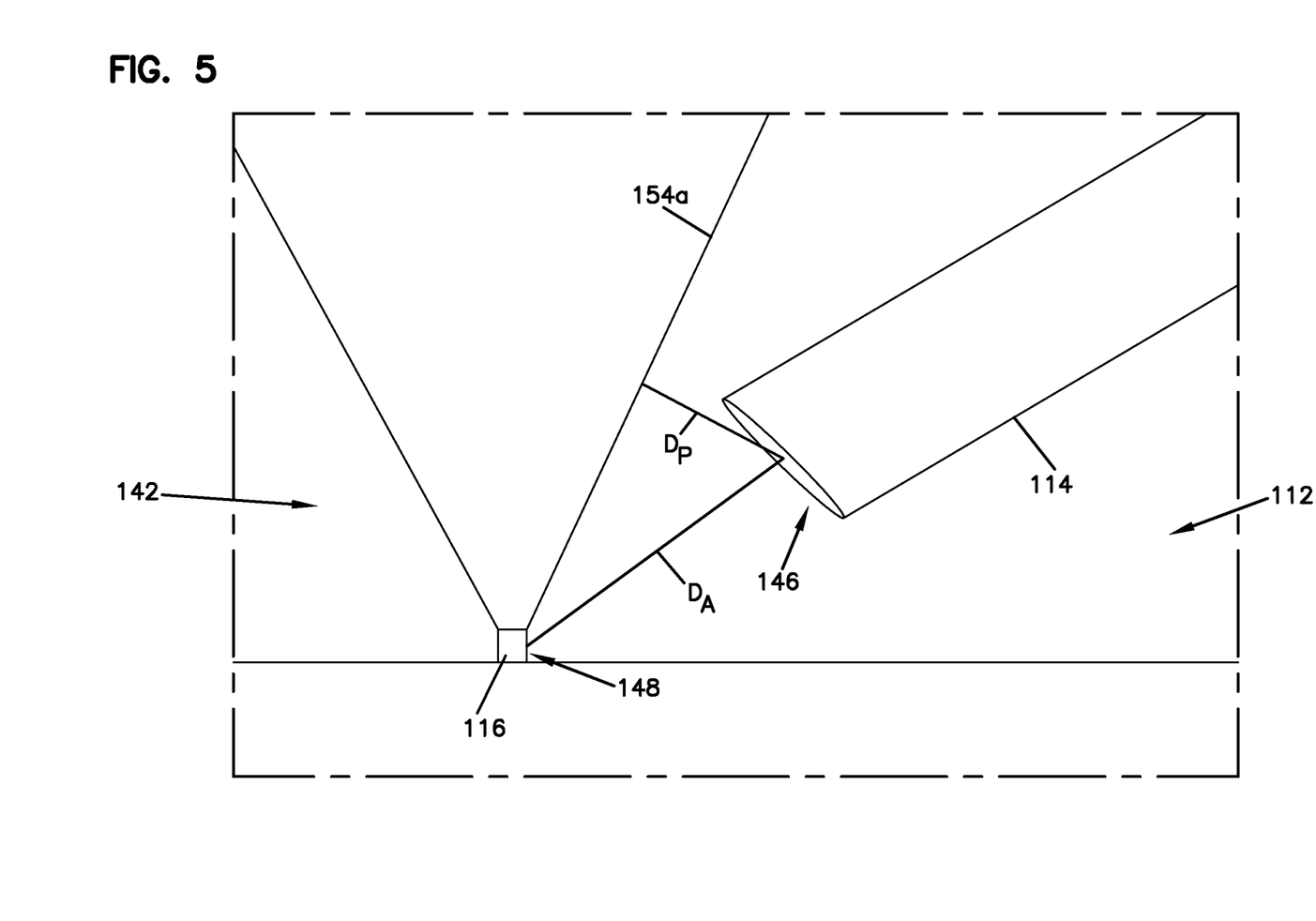
FIG. 5 is a view of the location of an embodiment of the sample injector of FIG. 2.

Referring to FIG. 5, an embodiment of the sample injector 114 is illustrated as positioned within an embodiment of the inlet chamber 112. Also shown is aperture 116. In the example shown, the outlet 146 of the sample injector 114 is disposed at a distance $D_P$ from the profile 154 and a distance $D_A$ from the inlet 148 of the aperture 116. Although other ranges are possible as well, in some embodiments, the sample injector 114 is disposed such that the distance $D_P$ is within one of the following ranges: 400 microns to 1200 microns, 500 microns to 1100 microns, 600 microns to 1000 microns, and 700 microns to 900 microns (or 800 microns+/−100 microns). In at least some of these embodiments, when the sample injector 114 is disposed within one of these ranges, the sample stream flow flows in biased proximity to the profile and provides spatial consistency of the particles entrained in the stream through the interrogation region 140 of the aperture 116. Additionally, in some embodiments, the sample injector is disposed such that the distance $D_A$ is within one of the following ranges: 1400 microns to 2200 microns, 1600 microns to 2000 microns, or 1650 microns to 1850 microns from the aperture inlet 148. In at least some of these embodiments, the distance $D_A$ is sufficient for the hydrodynamic effects to tighten the core of the sample stream prior to reaching the interrogation region 140. Accordingly, in one embodiment, the sample injector 114 is located 700 microns to 900 microns from the profile 154(a) and 1650 microns to 1850 microns from the inlet 148 of the aperture 116.

The sheath flow rate may be set to ensure laminar flow of the sheath fluid throughout the flow cell. In one embodiment, the sheath flow rate may be set between the ranges of 3-15 mL/min, 2-30 and 1-40 mL/min. As known in the art, the driving parameter is to maintain the Reynolds number of the fluid system below 2300 to avoid turbulent flow. And although the sheath flow rate may be higher or lower, in one embodiment, the sheath flow rate is set to 10 mL/min.

The sample stream rate as it exits the sample injector may be 0.1 μL/min to 200 μL/min while maintaining commercially acceptable coefficient of variation (CV) for measurement resolution. The commercially acceptable upper limit half-peak CV for spatial consistency of beads passing through the interrogation region 140 of the aperture 116 is 1.5%. By utilizing biased sample injectors as heretofore and hereafter described, a higher sample stream rate can be achieved while keeping the CV low as compared to conventional flow cells. Accordingly, a sample stream rate of 70 μL/min having a half-peak CV of 0.88% was achieved.

Figure 6:
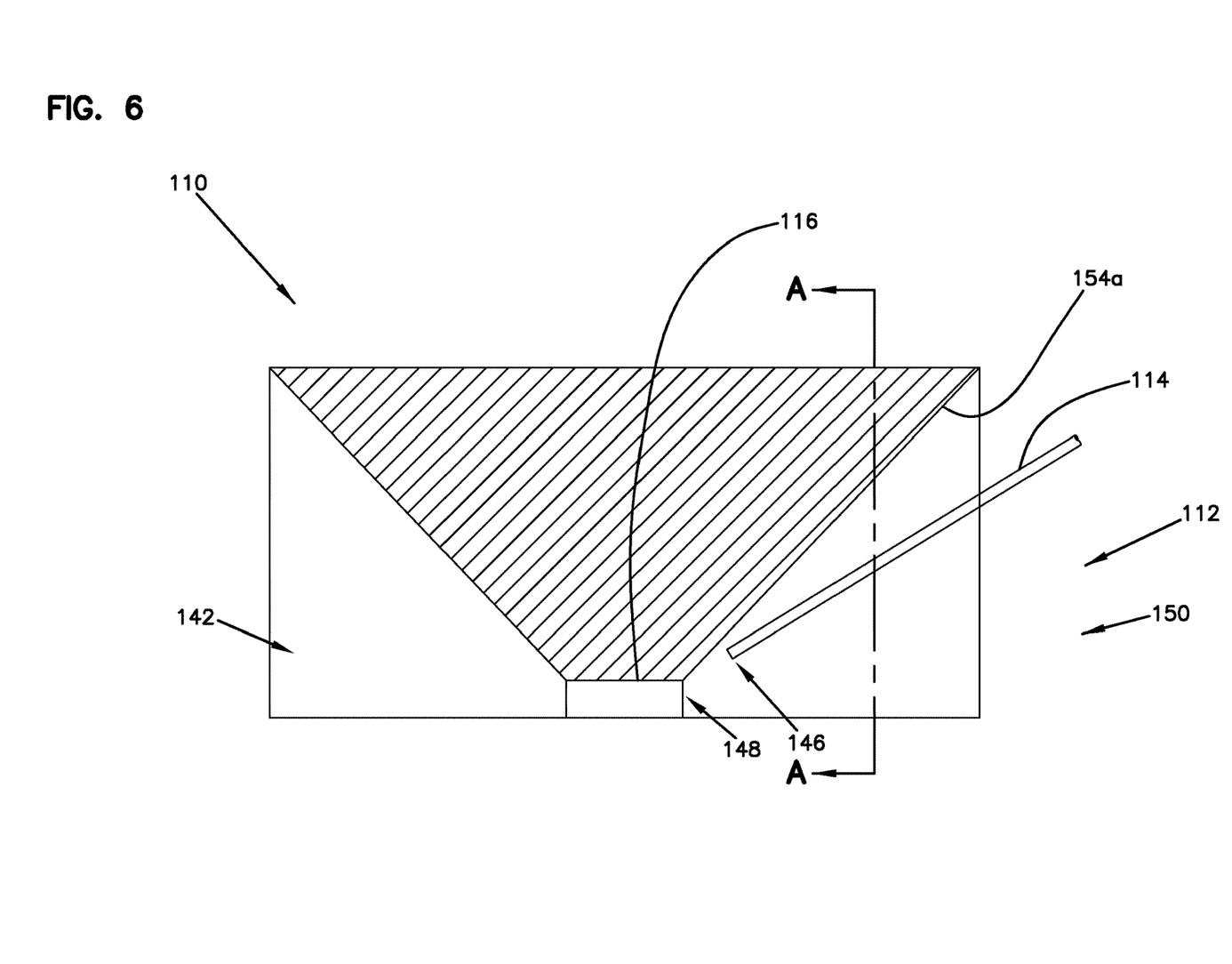
FIG. 6 is a schematic drawing of an embodiment of the flow cell of FIG. 2.

Turning to FIG. 6, a side view of an embodiment of the flow cell 110 is shown. In some embodiments, the inlet chamber 112 of the flow cell 110 has a tapered configuration. Examples of tapered configurations include tapered conical configurations, tapered rectangular configurations, tapered polygonal configurations, and other tapered shape configurations.

Figure 7:
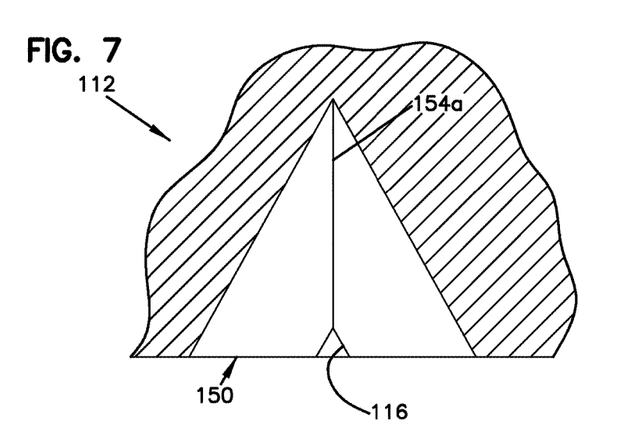
FIG. 7 illustrates an embodiment of the inlet chamber of FIG. 6.

FIG. 7 is a plan view through section A-A, and illustrates an embodiment that includes an aperture 116 having a triangular cross section and a three-sided pyramidal inlet chamber cavity 150. Also shown is profile 154(a). Other configurations of the profile and inlet chamber cavity are possible to practice the inventive aspects disclosed herein.

Figure 8:
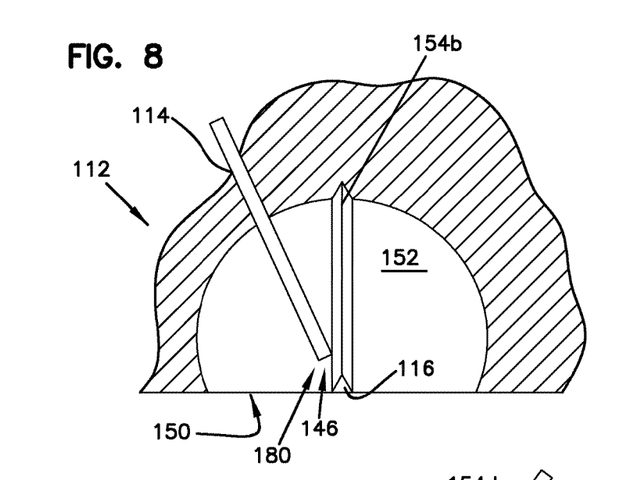
FIG. 8 illustrates another embodiment of the inlet chamber of FIG. 6.

In another embodiment as shown in FIG. 8, the cavity 150 of the inlet chamber 112 is generally a segment of a tapered conical configuration. The smaller end of the conical configuration leads to the aperture 116. In this embodiment, the profile 154(b) is a V-groove disposed in the chamber wall 152, wherein the profile 154(b) is directed toward the aperture 116. In other embodiments, the profile 154(b) is a V-groove built onto the chamber wall 152 or formed in a structure attached to or extending from the chamber wall 152. For example, in some embodiments, the profile 154(b) is formed on a protrusion on the chamber wall 152, between protrusions on the chamber wall 152, or formed in a channel disposed on the chamber wall 152.

Still referring to FIG. 8, the outlet 146 of the sample injector 114 is positioned off-center or asymmetrically at a position 180 in the inlet chamber 112 and biased towards the profile 154(b). In some embodiments, when positioned as shown, the sample stream from the sample injector 114 travels in biased proximity to the profile 154(b), and through the aperture 116, to obtain effective sample stream core compression.

Figure 9:
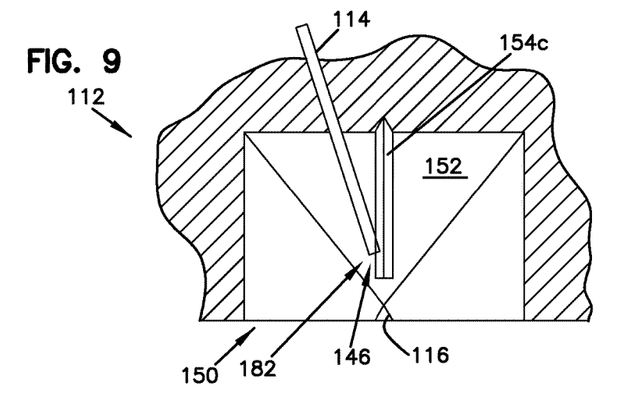
FIG. 9 illustrates another embodiment of the inlet chamber of FIG. 6.

In another embodiment as shown in FIG. 9, the cavity 150 of the inlet chamber 112 is generally a tapered rectangular configuration. The smaller end of the tapered rectangular configuration leads to the aperture 116. In this embodiment, the profile 154(c) is a V-groove disposed in the chamber wall 152, wherein the profile 154(c) is directed toward the aperture 116. In some embodiments, the V-groove is recessed in the chamber wall 152. In other embodiments, the profile 154(c) is a V-groove built onto the chamber wall 152 or formed in a structure attached to or extending from the chamber wall 152. For example, in some embodiments, the profile 154(c) is formed on a protrusion on the chamber wall 152, between protrusions on the chamber wall 152, or formed in a channel disposed on the chamber wall 152.

Still referring to FIG. 9, the outlet 146 of the sample injector 114 is positioned off-center or asymmetrically at a position 182 in the inlet chamber 112 and biased towards the profile 154(c), in some embodiments, when positioned as shown, the sample stream from the sample injector 114 travels in biased proximity to the profile 154(c), and through the aperture 116, to obtain effective sample stream core compression.

Figure 10:
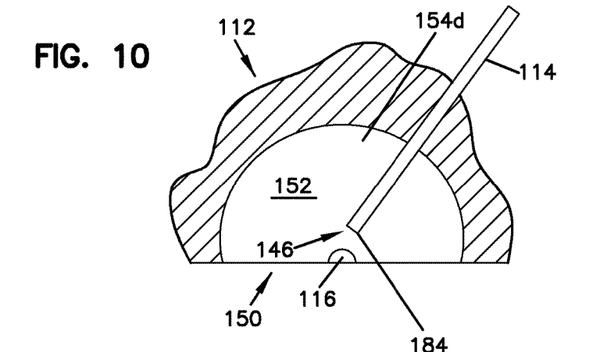
FIG. 10 illustrates another embodiment of the inlet chamber of FIG. 6.

In another embodiment as shown in FIG. 10, the cavity 150 of the inlet chamber 112 is generally a tapered conical configuration. The smaller end of the tapered conical configuration leads to the aperture 116. In this embodiment, the profile 154(d) is the chamber wall 152.

Still referring to FIG. 10, the outlet 146 of the sample injector 114 is positioned off-center or asymmetrically at a position 184 in the inlet chamber 112 and biased towards the profile 154(d). In some embodiments, when positioned as shown, the sample stream from the sample injector 114 travels in biased proximity to the profile 154(d), and through the aperture 116, to obtain effective sample stream core compression.

Figure 11:
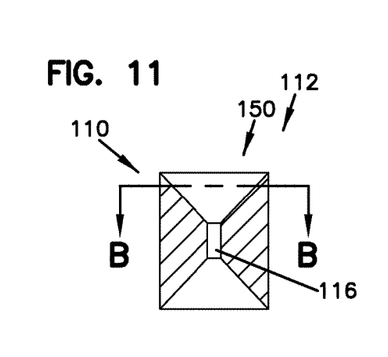
FIG. 11 is a schematic drawing of an embodiment of the flow cell of FIG. 2.

Although the embodiments disclosed in FIGS. 6-10 are arranged to have the sample stream travel generally in the horizontal direction through the flow cell 110, other embodiments may have a different orientation and may have a sample stream that travels in a different direction through the flow cell 110. For example, as shown in FIG. 11, the flow cell is arranged in a vertical orientation to allow flow of the sample stream through the aperture 116 in a vertical direction. In some embodiments, the cavity 150 of the inlet chamber 112 is generally a funnel-shaped configuration. The smaller end of the funnel-shaped configuration leads to the aperture 116. Alternate embodiments of features are shown in plan view of section B-B.

Figure 12:
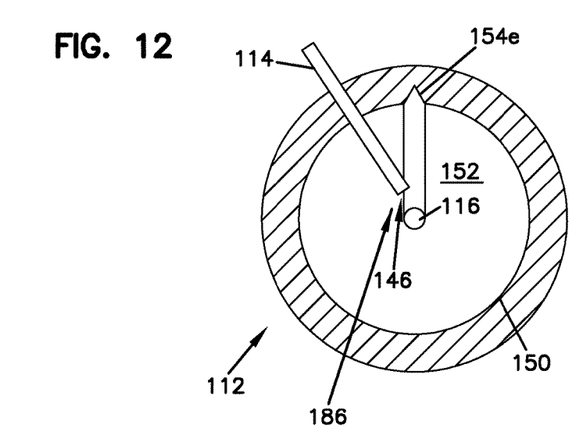
FIG. 12 illustrates an embodiment of the inlet chamber of FIG. 11.

In another embodiment as shown in FIG. 12, the cavity 150 of the inlet chamber 112 is generally a tapered conical configuration. The smaller end of the tapered conical configuration leads to the aperture 116. In this embodiment, the aperture 116 has a circular cross section, and the profile 154(e) is a V-groove disposed in the chamber wall 152, wherein the profile 154(e) is directed toward the aperture 116. In other embodiments, the profile 154(e) is a V-groove built unto the chamber wall 152 or formed in a structure attached to or extending from the chamber wall 152. For example, in some embodiments, the profile 154(e) is formed on a protrusion on the chamber wall 152, between protrusions on the chamber wall 152, or foil/led in a channel disposed on the chamber wall 152.

Still referring to FIG. 12, the outlet 146 of the sample injector 114 is positioned off-center or asymmetrically at a position 186 in the inlet chamber 112 and biased towards the profile 154(e). In some embodiments, when positioned as shown, the sample stream from the sample injector 114 travels in biased proximity to the profile 154(e), and through the aperture 116, to obtain effective sample stream core compression.

Figure 13:
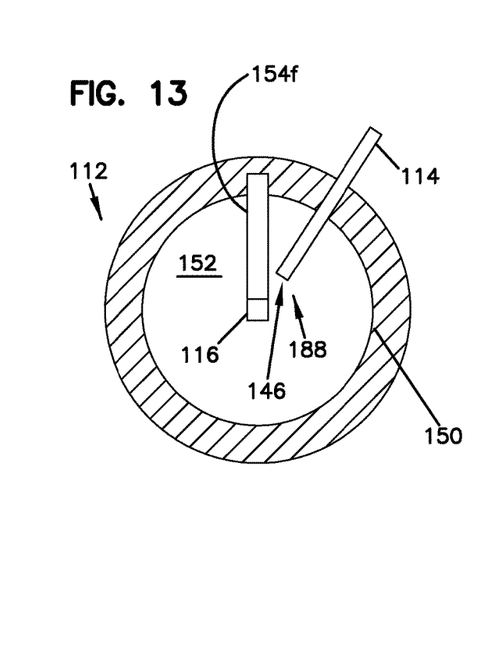
FIG. 13 illustrates another embodiment of the inlet chamber of FIG. 11.

In another disclosed embodiment as shown in FIG. 13, the cavity 150 of the inlet chamber 112 is generally a tapered conical configuration. The smaller end of the tapered conical configuration leads to the aperture 116. In this embodiment, the aperture 116 has a rectangular cross section, and the profile 154(f) is a rectangular channel disposed in the chamber wall 152, wherein the profile 154(f) is directed toward the aperture 116. In other embodiments, the profile 154(f) is a rectangular channel built onto the chamber wall 152 or formed in a structure attached to or extending from the chamber wall 152. For example, in some embodiments, the profile 154(f) is formed on a protrusion on the chamber wall 152 or between protrusions on the chamber wall 152.

Still referring to FIG. 13, the outlet 146 of the sample injector 114 is positioned off-center or asymmetrically at a position 188 in the inlet chamber 112 and biased towards the profile 154(f). In some embodiments, when positioned as shown, the sample stream from the sample injector 114 travels in biased proximity to the profile 154(f), and through the aperture 116, to obtain effective sample stream core compression.

Figure 14:
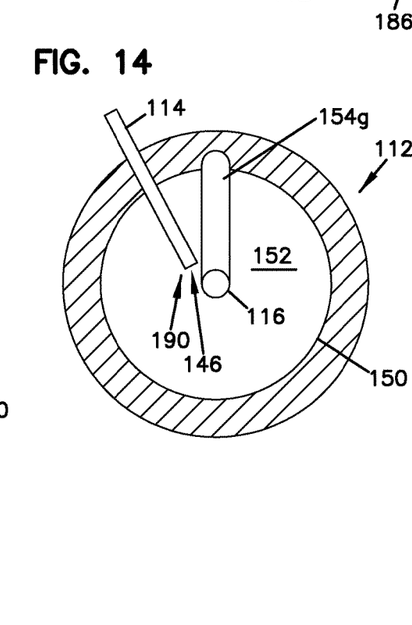
FIG. 14 illustrates another embodiment of the inlet chamber of FIG. 11.

In another embodiment as shown in FIG. 14, the cavity 150 of the inlet chamber 112 is generally a tapered conical configuration. The smaller end of the tapered conical configuration leads to the aperture 116. In this embodiment, the profile 154(g) is a channel having a semi-circular cross section disposed in the chamber wall 152, wherein the profile 154(g) is directed toward the aperture 116. In other embodiments, the profile 154(g) is a semi-circular channel built onto the chamber wall 152 or formed in a structure attached to or extending from the chamber wall 152. For example, in some embodiments, the profile 154(g) is formed on a protrusion on the chamber wall 152 or between protrusions on the chamber wall 152.

Still referring to FIG. 14, the outlet 146 of the sample injector 114 is positioned off-center or asymmetrically at a position 190 in the inlet chamber 112 and biased towards the profile 154(g). In some embodiments, when positioned as shown, the sample stream from the sample injector 114 travels in biased proximity to the profile 154(g), and through the aperture 116, to obtain effective sample stream core compression.

Figure 15:
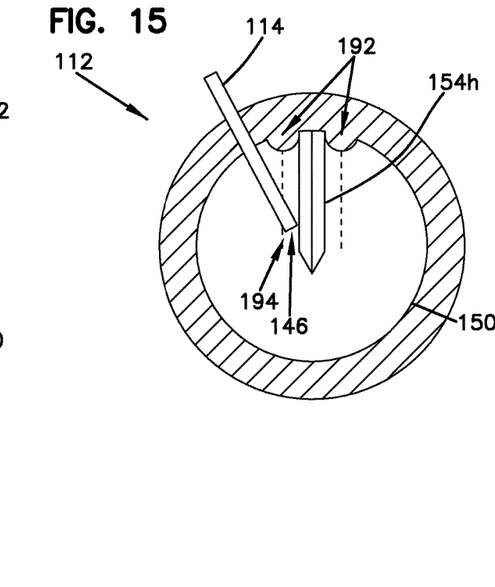
FIG. 15 illustrates another embodiment of the inlet chamber of FIG. 11.

In another embodiment as shown in FIG. 15, the cavity 150 of the inlet chamber 112 is generally a tapered conical configuration. The smaller end of the tapered conical configuration leads to the aperture 116. In this embodiment, the aperture 116 has a triangular cross section, and profile 154(h) is a feature formed by a pair of protrusions 192 extending into the cavity 150 of the inlet chamber 112, wherein the profile 154(h) is directed toward the aperture 116.

Still referring to FIG. 15, the outlet 146 of the sample injector 114 is positioned off-center or asymmetrically at a position 194 in the inlet chamber 112 and biased towards the profile 154(h). In some embodiments, when positioned as shown, the sample stream from the sample injector 114 travels in biased proximity to the profile 154(h), and through the aperture 116, to obtain effective sample stream core compression.

Figure 16:
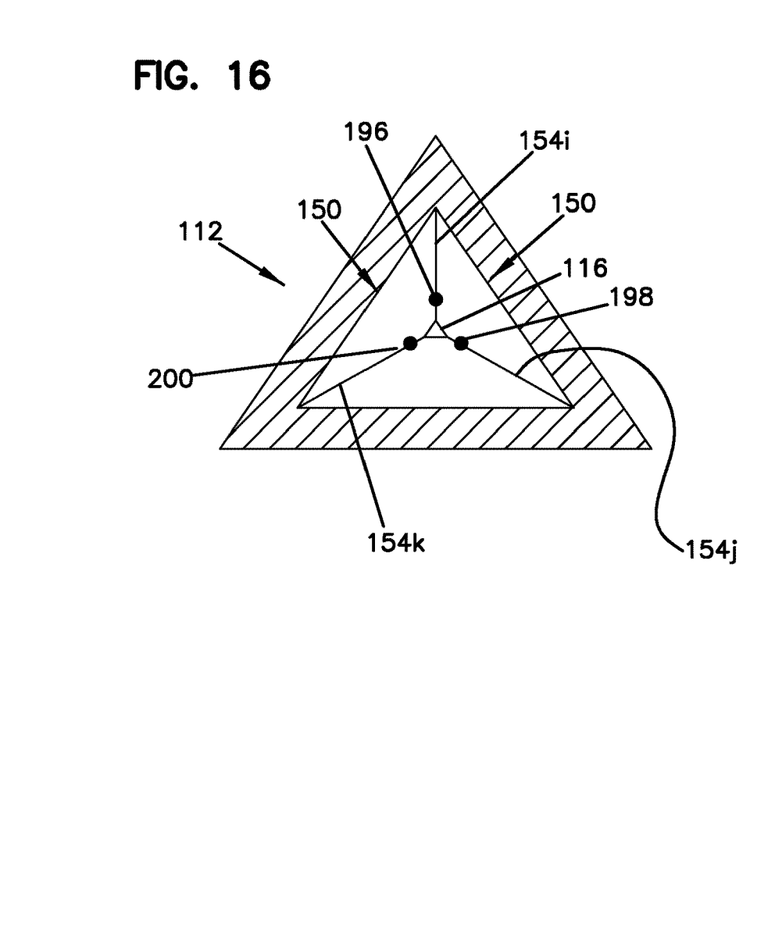
FIG. 16 illustrates another embodiment of the inlet chamber of FIG. 11.

In another disclosed embodiment as shown in FIG. 16, the cavity 150 of the inlet chamber 112 is generally an inverted three-sided pyramidal configuration. The smaller end of the inverted three-sided pyramidal configuration leads to the aperture 116. In this embodiment, the aperture 116 has a triangular cross section, and profile 154(i) is an edge of the inverted three-sided pyramidal configuration, wherein the profile 154(i) is directed toward the aperture 116.

Still referring to FIG. 16, the outlet 146 of the sample injector 114 is positioned off-center or asymmetrically at a position 196 in the inlet chamber 112 and biased towards the profile 154(i). In some embodiments, when positioned as shown, the sample stream from the sample injector 114 travels in biased proximity to the profile 154(i), and through the aperture 116, to obtain effective sample stream core compression. Sample injector 114 is not shown for clarity.

In yet another aspect of this disclosure, the flow cell 110 may include multiple profiles and multiple sample injectors. For example, the inlet chamber of FIG. 16 is a three-sided pyramidal form and includes three profiles 154(i), 154(j), 154(k) (i.e., the three edges formed by apexes of three pairs of planes). In this embodiment, multiple sample injectors may be positioned off-center or asymmetrically in the inlet chamber 112 and positioned biased in the direction of each profile 154(i), 154(j), 154(k), such as at the positions 196, 198, and 200 respectively (the sample injectors are not shown for clarity). In this way, the plurality of sample injectors may be disposed off-center or asymmetrically and biased in the direction of each of the plurality of profiles. Arranged this way, parallel sample ingestion onto the analyzer can be achieved. For example, a technician may load a first sample into the analyzer so that the sample will travel through a first sample injector, while a second sample travelling through a second sample injector 114 is being interrogated by the analyzer. In this way, loading samples may be accomplished while another sample is being interrogated. Accordingly, a more flexible and work efficient analyzer can thereby be achieved.

Figure 17:
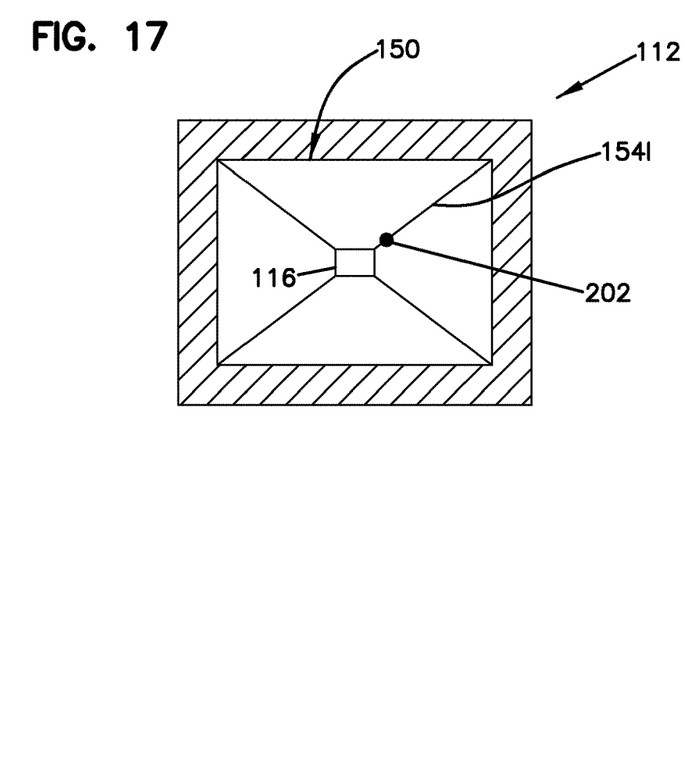
FIG. 17 illustrates another embodiment of the inlet chamber of FIG. 11.

In another embodiment as shown in FIG. 17, the cavity 150 of the inlet chamber 112 is generally an inverted four-sided pyramidal configuration. The smaller end of the inverted four-sided pyramidal configuration leads to the aperture 116. In this embodiment, the aperture 116 has a rectangular cross section, and profile 154(l) is an edge of the inverted four-sided pyramidal configuration, wherein the profile 154(l) is directed toward the aperture 116.

Still referring to FIG. 17, the outlet 146 of the sample injector 114 is positioned off-center or asymmetrically at a position 202 in the inlet chamber 112 and biased towards the profile 154(l). In some embodiments, when positioned as shown, the sample stream from the sample injector 114 travels in biased proximity to the profile 154(l), and through the aperture, to obtain effective sample stream core compression. The sample injector 114 is not shown for clarity. Similarly to the embodiment illustrated and described with reference to FIG. 16, a plurality of sample injectors may be included in the embodiment shown in FIG. 17 as well. For example, some embodiments include four sample injectors disposed in positions biased towards each of the profiles formed at the apexes of adjacent walls of the cavity 150.

Other embodiments, such as those illustrated and described with reference to FIGS. 6-15, may also include a plurality of profiles and a plurality of sample injectors disposed adjacent to the plurality of profiles in the inlet chamber 112. For example, various embodiments have multiple edges that may form profiles. Other profile configurations, such as V-grooves and channels can be disposed in several places along the inlet channel as well. Still further, a flow cell having multiple injectors can have a combination of sample stream flow in biased proximity to a flow and a sample stream flow in the middle of the inlet channel.

The different profile and inlet chamber embodiments disclosed herein can be mixed and matched. For example, a V-groove profile such as in the embodiment illustrated and described with respect to FIG. 8 may be arranged along the internal wall of an embodiment such as the three-sided pyramidal configuration illustrated and described with respect to FIG. 7. The rectangular channel profile illustrated and described in FIG. 13 may be disposed at a plurality of locations to form a multi-profiled inlet chamber similar to the embodiments illustrated and described with respect to FIGS. 16 and 17. Further, an inlet chamber may have a plurality of profiles having different configurations (e.g., a V-groove, an apex, a semi-circular channel, etc.).

Still further, the inlet chamber configuration may have other configurations. For example, the inlet chamber may generally be a funnel wherein the cross section, is circular, semicircular, triangular, polygonal, square or rectangular. The orientation of the inlet chamber may be vertical or horizontal or other orientations.

By positioning the sample injector in proximity to the profile in the inlet chamber, and having sheath fluid flowing from the inlet chamber to the aperture, the sample stream tends to travel in biased proximity to the profile thereby improving the tightening of the sample stream core without the need, for example, to overly narrow the diameter of the sample injector. The sample stream rate exiting the sample injector can be increased to while still effectively tightening the sample stream core and focusing the particles entrained therein in a spatially consistent manner through the interrogation zone.

The sample injector as disclosed herein may be a tube or a needle, made from one or more of glass, metal, plastic, or other suitable material.

The aperture 116 is a narrow passageway where the sample stream, in biased proximity to the profile, passes through the interrogating beam of light. As illustrated and described with respect to FIGS. 6-17, the cross-section of the aperture can be circular, triangular, rectangular, square, or any other suitable shape. The size of the cross-sectional sides can range from 25 to 1000 microns. In one embodiment, the cross section of the aperture 116 is a triangle having sides of 180 microns. The aperture can be encased in glass or quartz, or any other material with suitable optical clarity.

Figure 18:
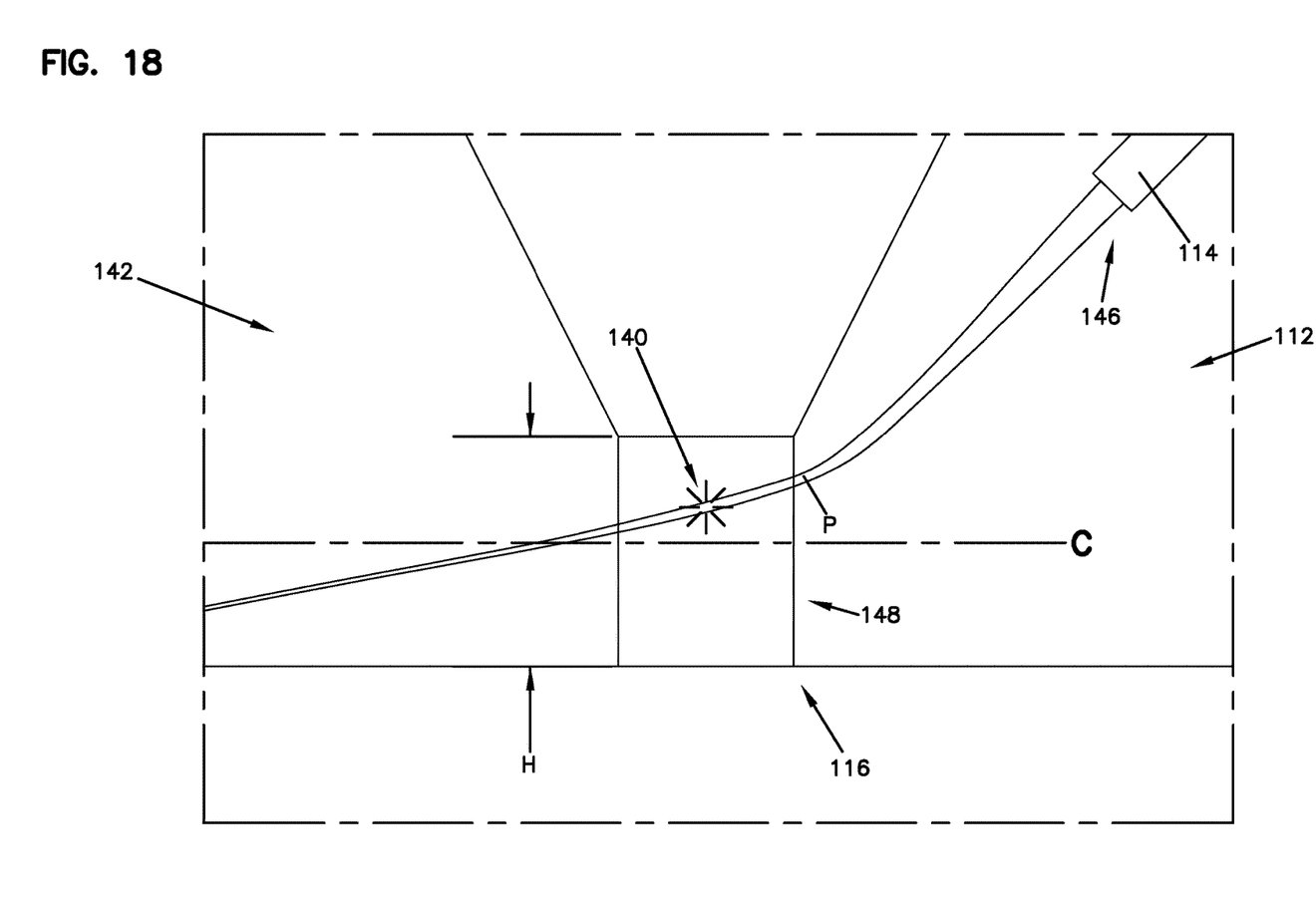
FIG. 18 is an expanded view of the interrogation region of an embodiment of the aperture of FIG. 2.

Referring to FIG. 18, the flow path P of the sample stream through the aperture is at least partially oblique to the longitudinal axis C of the aperture. This is a consequence of the sample stream traveling in biased proximity to a profile disposed along an internal surface of the inlet chamber. The sample stream transitions or turns to enter into the aperture flow. In the embodiment shown, the aperture 116 has a height H. In some embodiments, the height H is 150 µm.

Figure 19:
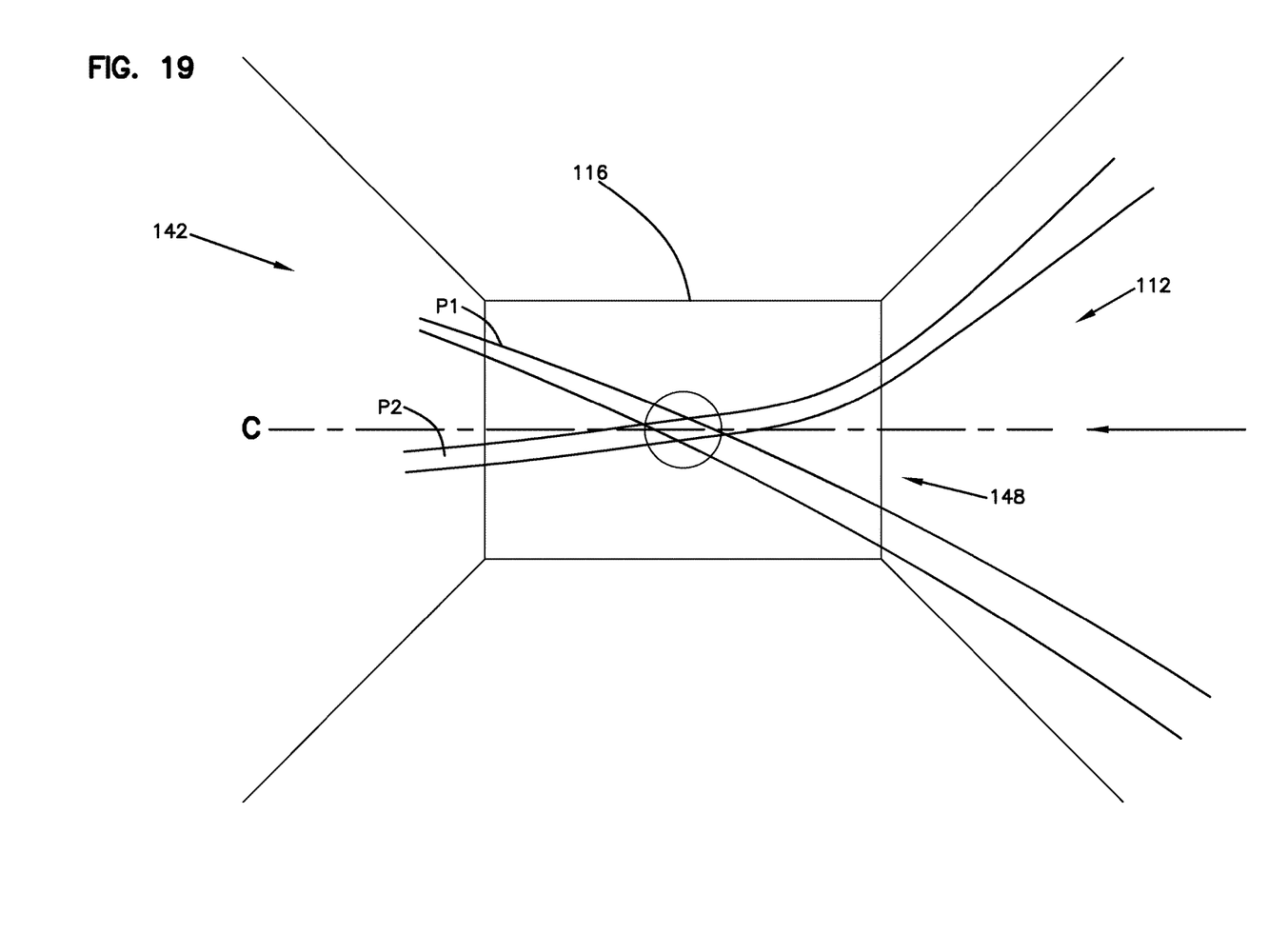
FIG. 19 is an expended view of the interrogation region of an embodiment of the aperture of FIG. 2 having multiple sample injectors.

In embodiments where multiple profiles and multiple sample injectors are arranged, as shown in FIG. 19, the at least partially oblique sample stream flow path from each of the sample streams (e.g., paths P1 and P2) can be arranged so that each share at least a portion of a path within the aperture. By focusing the interrogating light to the shared path region between sample streams, interrogation of the sample stream from either sample injector can be achieved. Moreover, where multiple sample streams are arranged to crossover or share a path within the aperture, interaction of the samples may be achieved and applications other than flow cytometry may be feasible such as rapid staining by having one stream containing particles and the other stream containing dye, causing chemical reactions where each stream has separate reaction constituents, and rapid mixing of sample streams.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A flow cell comprising:
   an aperture;
   an inlet chamber in fluid communication with the aperture, the inlet chamber having a triangular cross-sectional shape and formed by a bottom surface, a first side surface, and a second side surface, wherein the first and second side surfaces define an apex of the inlet chamber opposite the bottom surface, the inlet chamber suitable to contain sheath fluid; and
   a sample injector disposed in the inlet chamber to inject a sample into the inlet chamber and positioned closer to the apex of the inlet chamber than to the bottom surface, the injected sample forming a sample stream, the sample injector positioned such that the sample stream travels in biased proximity to the apex;
   wherein, the sample stream and sheath fluid in the inlet chamber flow through the aperture.

2. The flow cell of claim 1, wherein the apex is arranged at an edge of the first and second side surfaces, wherein the first and second side surfaces are planar.

3. The flow cell of claim 1, wherein the inlet chamber has a recessed V-groove disposed in a surface of the inlet chamber.

4. The flow cell of claim 1, wherein the inlet chamber has a channel formed along a surface of the inlet chamber.

5. The flow cell of claim 4, wherein the channel has a rectangular cross section.

6. The flow cell of claim 4, wherein the channel has a segment of a circular cross section.

7. The flow cell of claim 1, wherein the inlet chamber has a feature formed by protrusions on the interior wall of the inlet chamber.

8. The flow cell of claim 1, wherein the inlet chamber has a V-groove formed between protrusions on a surface of the inlet chamber.

9. The flow cell of claim 1, wherein the sample injector is positioned asymmetrically in the inlet chamber and biased in the direction of the apex.

10. The flow cell of claim 1, wherein the sample stream flows through the aperture at least partially oblique to a longitudinal axis of the aperture.

11. A flow cell comprising:
   an aperture;
   an inlet chamber in fluid communication with the aperture, the inlet chamber having a triangular cross-sectional shape and formed by a first surface, a second surface, and a third surface, wherein the first and second surfaces define an apex of the inlet chamber opposite the third surface; and a sample injector disposed in the inlet chamber to inject a sample into the inlet chamber, the injected sample forming a sample stream, the sample injector positioned off-center within the inlet chamber and closer to the apex of the inlet chamber than to the third surface.

12. The flow cell of claim 11, wherein the sample stream flows through the aperture at least partially oblique to the longitudinal axis of the aperture.

13. The flow cell of claim 11, wherein the sample includes particles suspended in fluid.

14. The flow cell of claim 11, wherein the inlet chamber is generally a three sided pyramidal configuration.

15. The flow cell of claim 14, wherein the inlet chamber is a tapered configuration.

16. The flow cell of claim 11, wherein the aperture cross section is one of circular, triangular, and rectangular cross section.

17. A method of interrogating a sample comprising:

causing a sheath fluid to flow into an inlet chamber and through an aperture, the inlet chamber having a triangular cross-sectional shape and having a bottom surface, a first side surface, and a second side surface, wherein the first and second side surfaces define an apex of the inlet chamber opposite the bottom surface;

injecting the sample into the inlet chamber with a sample injector to form a sample stream that is entrained in the sheath fluid, wherein an outlet of the sample injector is disposed in an off-center position within the inlet chamber and closer to the apex of the inlet chamber than to the bottom surface; and interrogating the sample stream as the sample stream passes through an interrogation region within the aperture.

18. The method of claim 17, wherein the outlet of the sample injector is biased in a direction of the apex of the inlet chamber.

19. The method of claim 17 further comprising:

injecting a second sample into an inlet chamber with a second sample injector to form a second sample stream that is entrained in the sheath fluid, wherein an outlet of the second sample injector is disposed in an off-center position within the inlet chamber; and interrogating the second sample stream as the second sample stream passes through the interrogation region within the aperture.

20. The flow cell of claim 1, wherein the sample injector is directed above a center of the aperture, relative to the bottom surface.

* * * * *